(12) United States Patent
Strobl

(10) Patent No.: US 10,946,224 B2
(45) Date of Patent: Mar. 16, 2021

(54) MULTI-STAGE NASAL FILTER AND METHOD OF TUNING THE FILTER TO A PREDETERMINED MOST PENETRATING PARTICLE SIZE

(71) Applicant: Frederick Thomas Strobl, Scottsdale, AZ (US)

(72) Inventor: Frederick Thomas Strobl, Scottsdale, AZ (US)

( * ) Notice: Subject to any disclaimer, the term of this patent is extended or adjusted under 35 U.S.C. 154(b) by 0 days.

(21) Appl. No.: 16/806,857

(22) Filed: Mar. 2, 2020

(65) Prior Publication Data

US 2021/0008397 A1     Jan. 14, 2021

Related U.S. Application Data

(63) Continuation-in-part of application No. 16/703,707, filed on Dec. 4, 2019.

(60) Provisional application No. 62/873,209, filed on Jul. 12, 2019.

(51) Int. Cl.
*A62B 23/06* (2006.01)
*A61M 16/10* (2006.01)
*A61M 16/00* (2006.01)

(52) U.S. Cl.
CPC ......... *A62B 23/06* (2013.01); *A61M 16/0087* (2013.01); *A61M 16/105* (2013.01); *A61M 2202/005* (2013.01); *A61M 2205/02* (2013.01); *A61M 2205/7509* (2013.01); *A61M 2207/10* (2013.01)

(58) Field of Classification Search
CPC ......... A62B 23/00; A62B 23/02; A62B 23/06; A61M 16/00; A61M 16/06; A61M 16/0666; A61M 16/105; A61M 2205/0205; A61M 2016/0661; A61M 2209/06; A61M 2207/10
See application file for complete search history.

(56) References Cited

U.S. PATENT DOCUMENTS

| 2,162,583 A | 6/1939 | Ktellsson |
| 3,457,917 A | 7/1969 | Mercurio |
| 3,463,149 A | 8/1969 | Abu |

(Continued)

FOREIGN PATENT DOCUMENTS

| WO | WO 2017089912 | 1/2017 |
| WO | WO 2018158781 | 9/2018 |

OTHER PUBLICATIONS

X. Qin, S.Subianto, "Electrospun Nanofibers" 2017, Woodhead Publishing Series in Textiles, pp. 449-466 (Year: 2017).*

(Continued)

*Primary Examiner* — Bradley H Philips
*Assistant Examiner* — Savannah L Gabriel
(74) *Attorney, Agent, or Firm* — Jennings, Strouss & Salmon PLC; Daniel R. Pote

(57) ABSTRACT

Respiratory devices and methods for their manufacture and use are disclosed. The device features a resiliently deformable element configured to form a perimeter seal with the inner nostril wall and to swab the distal portion of the internal nostril region with a disinfectant during device installation. A first filter stage includes a first filter layer characterized by first geometric convolutions and a first MPPS1 value; and a second filter stage includes a second filter layer characterized by second geometric convolutions and a second MPPS2 value.

11 Claims, 5 Drawing Sheets

(56) References Cited

U.S. PATENT DOCUMENTS

| | | | |
|---|---|---|---|
| 4,052,983 A * | 10/1977 | Bovender | A62B 23/06 |
| | | | 128/204.12 |
| 4,267,831 A * | 5/1981 | Aguilar | A61M 15/085 |
| | | | 128/203.14 |
| 4,856,509 A * | 8/1989 | Lemelson | A41D 13/1146 |
| | | | 128/206.19 |
| 5,417,205 A | 5/1995 | Wang | |
| 5,425,359 A | 6/1995 | Liou | |
| 5,568,808 A | 10/1996 | Rimkus | |
| 5,890,491 A | 4/1999 | Rimkus | |
| 5,890,791 A * | 4/1999 | Saito | G02B 6/0053 |
| | | | 362/330 |
| 6,119,690 A | 9/2000 | Pataleo | |
| 6,494,205 B1 | 12/2002 | Brown | |
| 7,735,491 B2 * | 6/2010 | Doshi | A61M 15/08 |
| | | | 128/207.18 |
| 7,918,224 B2 | 4/2011 | Dolezal | |
| 10,322,304 B2 | 5/2019 | Kronenberg | |
| 2003/0106556 A1 | 6/2003 | Alperovich et al. | |
| 2003/0209145 A1 | 11/2003 | Soper | |
| 2005/0066972 A1 | 3/2005 | Michels | |
| 2005/0150385 A1 | 7/2005 | Huang et al. | |
| 2007/0277832 A1 * | 12/2007 | Doshi | A61M 16/0688 |
| | | | 128/207.18 |
| 2009/0007919 A1 | 1/2009 | Dolezal et al. | |
| 2009/0320849 A1 | 12/2009 | Biedermann | |
| 2010/0307119 A1 | 12/2010 | Leung et al. | |
| 2012/0060842 A1 | 3/2012 | Curtis | |
| 2012/0097177 A1 * | 4/2012 | Boothe | A61F 11/06 |
| | | | 128/864 |
| 2012/0279504 A1 * | 11/2012 | Moore | A62B 23/06 |
| | | | 128/206.11 |
| 2013/0184684 A1 | 7/2013 | Yardley | |
| 2015/0238785 A1 * | 8/2015 | Chuang | A62B 23/06 |
| | | | 128/202.27 |
| 2016/0220854 A1 | 8/2016 | Kronenberg et al. | |
| 2017/0128515 A1 * | 5/2017 | Willimann | A61K 31/045 |
| 2017/0361023 A1 | 12/2017 | Anderson et al. | |
| 2018/0304108 A1 | 10/2018 | Curtis | |
| 2019/0070441 A1 * | 3/2019 | Archouniani | A62B 23/06 |
| 2019/0126023 A1 * | 5/2019 | Bryzek | A46B 9/04 |

OTHER PUBLICATIONS

Lisa Brosseau & Roland Berry Ann,"N95 Respirators and Surgical Masks",CDC, Oct. 4, 2009, 60pgs.

Ramazan Azmatula & Wasum Khan, "Synthesis and applications of Electrospun Nanofibers", Science Direct 2019, sciencedirect.com, 2pgs, pdf of Abstract.

Trevor Sparks & George Chase, "Filter Media", Filters and Filtration Handbook, Sixth Edition (2016), pp. 55-115 (in handbook), 2pgs, pdf of Abstract.

* cited by examiner

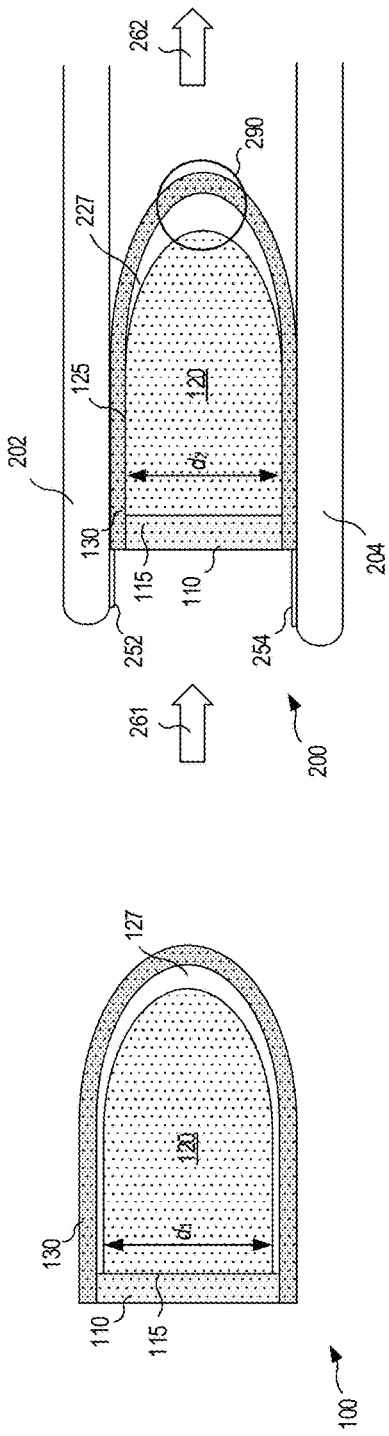
FIG. 1
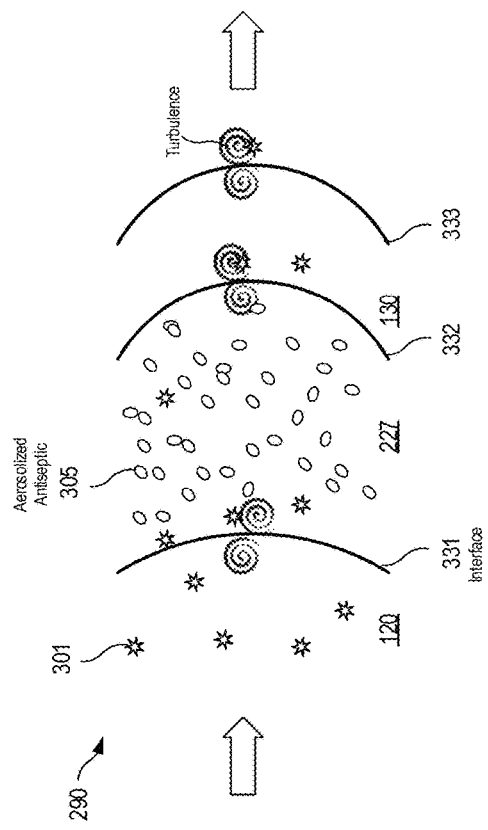
FIG. 2
FIG. 3

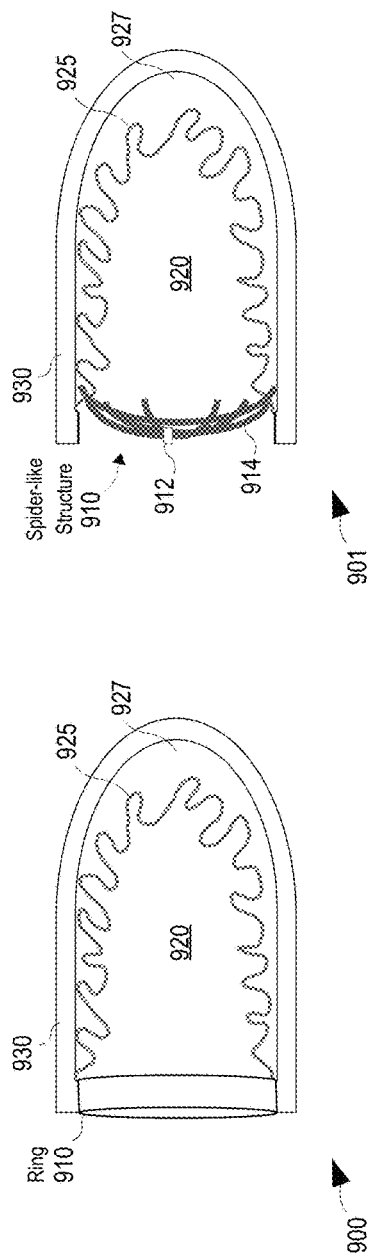
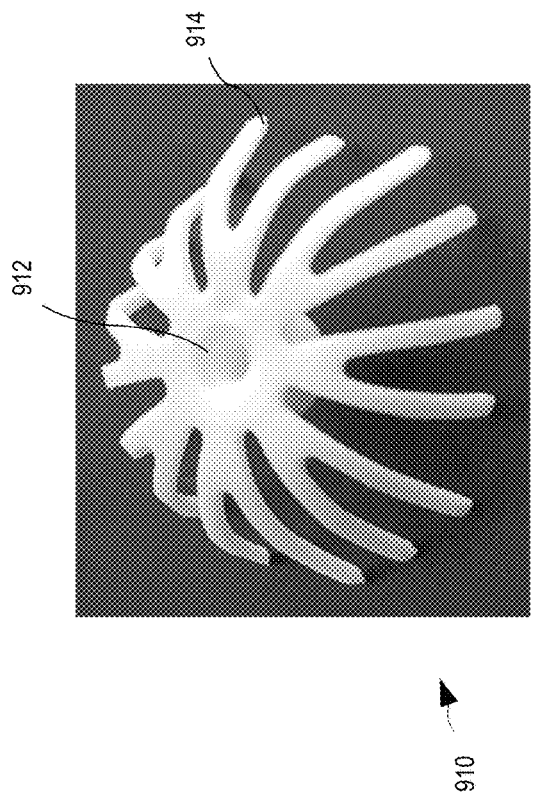
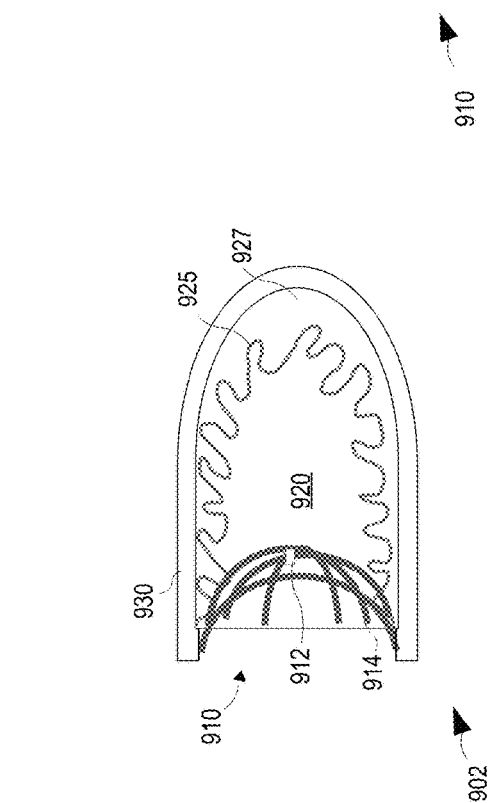
FIG. 9
FIG. 10A
FIG. 10B
FIG. 11

MULTI-STAGE NASAL FILTER AND METHOD OF TUNING THE FILTER TO A PREDETERMINED MOST PENETRATING PARTICLE SIZE

PRIORITY CLAIM

This non-provisional continuation-in-part application claims priority to U.S. patent application Ser. No. 16/703,707 filed Dec. 4, 2019 and U.S. provisional application Ser. No. 62/873,209 filed Jul. 12, 2019, the entire contents of which are hereby incorporated by this reference.

TECHNICAL FIELD

The present disclosure generally relates to a multi-stage filtration device insertable into human nostrils for filtering allergens and pathogens from inhaled ambient air and, more particularly, to a device having first and second stage filter materials exhibiting first and second Most Penetrating Particle Size (MPPS) values, respectively.

BACKGROUND OF THE DISCLOSURE

Recent outbreaks of infectious disease have proven state of the art response protocols to be wholly inadequate, including efforts at containment, quarantine, information dissemination, vaccine development, and travel restrictions. Influenza epidemics such as SARS (Severe Acute Respiratory Syndrome) in 2003, H1N1 in 2011, avian in 2015, and the Coronavirus of 2020 share the same transmission modality—airborne particulates. Presently known face masks and nasal filters employ structural features supporting filter materials exhibiting mean pore sizes designed to remove (filter) relatively large particles such as dust, smog, pollen, and allergens from the inhaled airstream. However, these devices are less effective against the smaller particle sizes which characterize the Coronavirus and other strains of influenza (e.g., 0.1-0.3 microns).

For example, Albu U.S. Pat. No. 3,463,149 discloses a filter plug comprising a cotton body contained within a fabric covering. A medicament containing cylinder, having a stationary ported piston received therein, dispenses medicament into the body upon relative movement of the cylinder and piston.

Kronenberg U.S. Pat. No. 10,322,304 B2 discloses a two-stage filter system including a microfiber filter and a nanofiber filter used in series, with the nanofiber filter located downstream of the microfiber filter.

Dolezal U.S. Pat. No. 7,918,224 B2 discloses a pair of ellipsoidal filters exhibiting a corrugated structure to increase the surface area available for filtration.

Fiber-based filter materials are sometimes characterized by a "most penetrating particle size" (MPPS), which refers to that certain particle size (or range) against which the traditional mechanical filtering mechanisms (interception, impaction, and diffusion) are least effective. If the material exhibits high performance at a particular MPPS value, then particles both larger and smaller than this value will be collected with even higher performance. ("N95 Respirators and Surgical Masks", by Lisa Brosseau and Roland Berry Ann, Centers for Disease Control and Prevention (Oct. 14, 2009)).

The Albu, Kronenberg, Dolezal, Brosseau, and the other patent and non-patent references cited herein are hereby incorporated in their entirety.

Presently known filter devices are unsatisfactory in several regards. For example, gaps form between the device and the surrounding nasal walls, creating a local low resistance path through which at least some portion of the inhaled air stream escapes around the "seal" formed between the outer perimeter of the filter and the internal perimeter of the adjacent nasal surfaces. To at least this extent, the bypass stream passes through the trachea into the lungs unfiltered.

Longstanding and accepted design practices recognize that the high impedance materials used in face masks are not well suited for intranasal use. That is, the 20-30 square inch surface area of a high impedance mask does not appreciably inhibit normal breathing. However, drawing the same volume of air through a conventional nasal filter having a surface area in the range of 0.25 in$^2$ would be physically impossible for most people. Presently known nasal filter designs therefor eschew high impedance filter materials in favor of lower impedance materials which exhibit correspondingly higher MPPS values. Consequently, very small particle sizes in the 0.1-0.3 micron range pass through the nasal filter and enter the body, potentially causing infection.

Nasal filter devices and systems are thus needed which overcome these and other shortcomings of the prior art.

SUMMARY OF THE DISCLOSURE

Various embodiments of the present invention involve a single or multistage nasal filter device characterized by respective first and second most penetrating particle size values (MPPS1 and MPPS2) in a single layer or in two or more layers (or stages) of filter material. In this way, a "generic" device structure may be configured to support any number of different applications or use cases. That is, the same base nasal device may function as a template to support different combinations of stages, filter layers, and filter materials of different sizes, shapes, geometries, relative positions, and MPPS values. Moreover, various combinations and sub-combinations of the foregoing parameters may be optimized to tune the resulting device to one or more specific particle sizes (or ranges).

Various embodiments of the present invention involve a single or multistage nasal filter device characterized by respective first and second most penetrating particle size values (MPPS1 and MPPS2) in a single layer or in two or more layers (or stages) of filter material. In this way, a "generic" device structure may be configured to support any number of different applications or use cases. That is, the same base nasal device may function as a template to support different combinations of stages, filter layers, and filter materials of different sizes, shapes, geometries, relative positions, and MPPS values. Moreover, various combinations and sub-combinations of the foregoing parameters may be optimized to tune the resulting device to one or more specific particle sizes (or ranges).

Other embodiments involve materials, specifications, and manufacturing processes such as electrospinning with or without aerogel to generate micropores and macropores using silica nanospheres in a cage structure to create filter media which exhibits the desired MPPS value or values. These techniques and resulting materials can be used to either augment or replace the use of woven fabric to yield the sieve type pore structures used today. Other embodiments involve design metrics and assembly techniques for configuring these filter materials such that the overall device has a sufficiently low aggregate impedance to avoid discomfort, notwithstanding the high intrinsic impedance of some of the material components.

Other embodiments involve arranging the high impedance material layers such that they exhibit an effective surface area far greater than the cross-sectional area of a typical nasal passage. For example, by folding or otherwise imparting pleats, undulations, bellows, or other regular or irregular geometric features or patterns into the material, the effective impedance may be substantially reduced (relative to a planar sheet positioned orthogonal to the direction of airflow), while still maintaining the benefits of low MPPS values. That is, rather than employing a two dimensional planar filter layer, the present inventions proposed to expand the layer into three spatial dimensions to thereby increase the effective surface area and reduce the effective impedance of the layer.

Other advantages of the invention surround exploiting various synergies resulting from: i) selectively configuring MPPS values for one or more filter layers; ii) using electrospinning or other material fabrication techniques to produce the filter materials with the desired mechanical (MPPS) and chemical characteristics, either in addition to or in lieu of conventional woven fabric filter materials and the conventional manufacturing techniques used to produce them; iii) superimposing geometric convolution onto the filter layer(s) to mitigate the impedance issues presented by the low particle size MPPS values; and iv) optimizing the foregoing in a single stage or multiple stages to thereby tune the device a particular particle size or sizes; v) embedding into or coating the surfaces of some of the foregoing components with an antiseptic which causes the user to swab the distal region of the nasal mucosa while inserting the device into the nose; and vi) designing a structural nasal filter template or frame which fits securely and comfortably inside the nose, but which can be adapted to—or tuned to—different particle sizes or "set points" by using different combinations of filter materials.

Various embodiments of the present disclosure relate to single stage nasal filters and other embodiments relate to multi-stage nasal filters. Various embodiments a first stage filter material exhibiting a first MPPS value and a second stage filter material exhibiting a second MPPS value, wherein at least one of the materials is convoluted or otherwise configured in three spatial dimensions to reduce the effective impedance of the filter stage. Other embodiments employ electrospun materials to facilitate tuning one or more MPPS values associated with one or more filter stages, respectively, to a desired particle size or sizes. Other embodiments include a pair of single or multi-stage filters connected by a band (e.g., 0.25-1 mm cross-section) to facilitate manual removal, where the initial (first) stage has a smaller pore size (or MPPS value) than the intermediate (second) stage, and the final (third) stage has a smaller pore size (or MPPS value) than the first and second stages. One or more stages may exhibit electrostatic properties and/or be coated (or saturated) with an antiseptic or disinfectant such as povidone iodine or iodoprovidone, commonly marketed under the brand name Betadine™ or silver.

The shape and size of adjacent stages (e.g., the second and third stages) may be configured to induce venturi-type turbulence proximate the stage 2/stage 3 interface, causing increased contact between particulates and the antiseptic borne by the filter fibers. For example, eddy currents resulting from turbulent air flow may cause pathogens to contact (and thus be killed by) antiseptic borne by one or more of:
i) the distal surface of the second stage filter;
ii) the proximal surface of the second stage filter;
iii) internal passages within the second stage filter;
iv) the distal surface of the third stage filter;
v) the proximal surface of the third stage filter;
vi) internal passages within the third stage filter;
vii) aerosolized antiseptic proximate the distal surface of the second stage filter;
viii) aerosolized antiseptic proximate the proximal surface of the second stage filter;
ix) aerosolized antiseptic proximate the distal surface of the third stage filter;
x) aerosolized antiseptic proximate the proximal surface of the third stage filter; and/or
xi) aerosolized antiseptic within the space between the second and third stage filters.

In an embodiment, the second stage comprises a resiliently deformable foam-type material having slightly larger cross-section than the nasal passage within which it is disposed. The third stage comprises a sheet or blanket of fabric loosely enveloping the second stage and forming an air gap therebetween. Once the assembly is inserted into the nostril, the second stage resiliently expands to synchronously urge both the second and third stages against the internal surfaces of the septum and nares, forming a perimeter seal. In this way, as the "oversized" assembly is inserted into the distal portion of the nasal passage, the exposed mucosa is swabbed with antiseptic. This swabbing effectively kills any pathogenic particulates which might otherwise enter the body through the distal mucosa located "upstream" of the inserted filter assembly.

A further embodiment contemplates a sealed package (e.g., plastic, foil) which contains a single or multi-stage nasal filter immersed in an aqueous antiseptic environment. The sealed package maintains sterility of the device prior to insertion, and also ensures that the filter materials (e.g., cotton, foam, fabric) remain saturated with antiseptic solution until used. This also ensures that the distal mucosa will be liberally swabbed during insertion, without the need for supplemental swabbing.

BRIEF DESCRIPTION OF THE DRAWING FIGURES

A more complete understanding of the embodiments of the present disclosure may be derived by referring to the detailed description and claims when considered in connection with the following illustrative figures, and:

FIG. 1 is a schematic cross-section view of a multi-stage filter prior to nasal insertion in accordance with various embodiments;

FIG. 2 is a schematic cross-section view of the multi-stage filter subsequent to nasal insertion in accordance with various embodiments;

FIG. 3 is a detail schematic cross-section view of venturi-type turbulence proximate stages 2 and 3 in accordance various embodiments;

Figure 7:
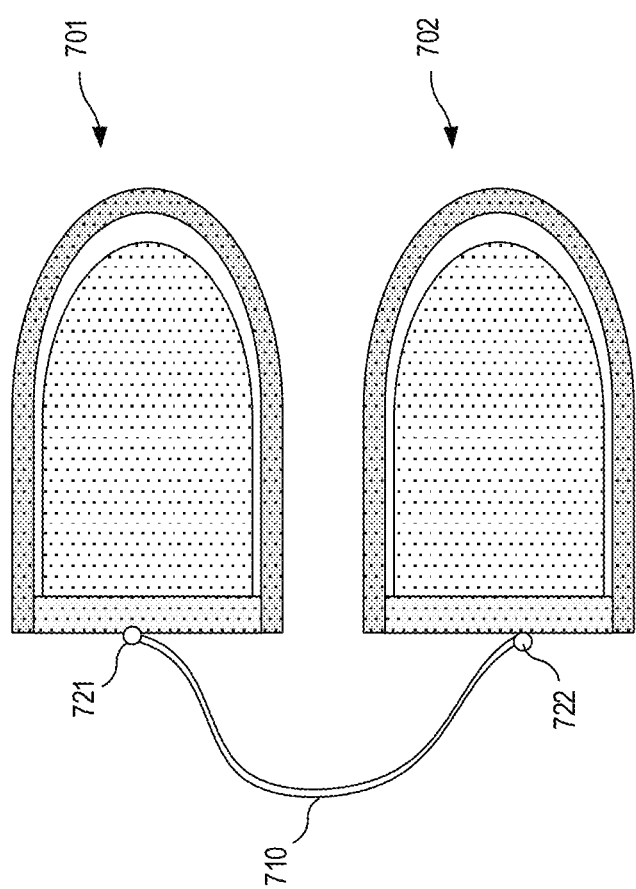
Figure 8:
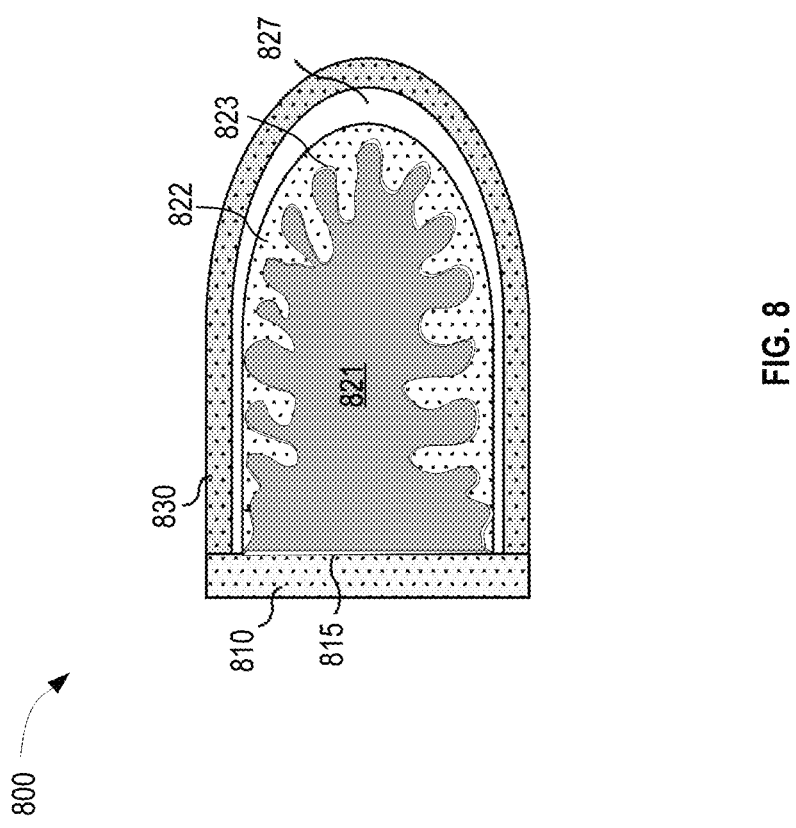

FIG. 6 A is a perspective view of a sealed package containing a nasal filter saturated in an aqueous antiseptic solution in accordance with various embodiments;

FIG. 6 B is a perspective view of the package of FIG. 6 A torn open to reveal the saturated nasal filter in accordance with various embodiments;

FIG. 7 is a cross section view of a pair of filters interconnected by a band;

FIG. 8 is a schematic cross-section view of an alternate embodiment of a multi-stage filter wherein the second stage comprises a hollow interior defining a plurality of concave finger-like geometric convolutions in accordance with various embodiments;

FIG. 9 is a schematic cross-section view of a further embodiment of the multi-stage filter of FIG. 8, wherein the second stage comprises a "solid" interior terminating in a plurality of convex convolutions in accordance with various embodiments;

FIG. 10A is a schematic cross-section view of an alternate embodiment of a multi-stage filter similar to FIG. 8 or 9, including a resiliently expandable claw disposed with its convex region extending in the distal direction of the nasal passage in accordance with various embodiments;

FIG. 10B is a schematic cross-section view of an alternate embodiment of a multi-stage filter similar to FIG. 10, with the resiliently expandable claw disposed with its concave region extending in the distal direction of the nasal passage in accordance with various embodiments; and FIG. 11 is perspective view of the claw shown in FIG. 10.

It will be appreciated that elements in the figures are illustrated for simplicity and clarity and have not necessarily been drawn to scale. For example, the dimensions of some of the elements in the figures may be exaggerated relative to other elements to enhance clarity of the accompanying descriptions of various illustrated embodiments. Moreover, although various embodiments are illustrated in the context of a single device to be inserted into a single nostril, those skilled in the art will appreciate that each single filter assembly comprises one of a pair of identical or mirror image filters configured to be inserted into both nostrils.

DETAILED DESCRIPTION OF EXEMPLARY EMBODIMENTS

Various embodiments of the disclosure involve filter materials which may be characterized by either a pore size which generally corresponding to the smallest particle captured by the material, or a "most penetrating particle size" (MPPS) value which refers to a particle size at which the material is least efficient. That is, if a material demonstrates high performance (i.e., high filtering efficiency) at a particular MPPS value, then the material will collect particles both larger and smaller than the MPPS value at even higher performance. The present inventor has determined that both woven and non-woven material filter materials may be effectively "tuned" to one or more MPPS values by using small diameter fibers (e.g., submicron and nano-fibers) manufactured using techniques such as electrospinning, force spinning, and fiber splitting. (See, "Synthesis and Applications of Electrospun Nanofibers" by Ramazan Azmatula and Waseem Khan (ScienceDirect 2019); and "Filter Media" by Trevor Sparks and George Chase, Filters and Filtration Handbook (Sixth Edition) (2016).)

Sub-micron and nano-fibers may be used in the context of various embodiments to "tune" filter materials to one or more particular MPPS values, for example in the range of 0.001-100 microns, and alternatively in the range of 0.05-20 microns, such as 0.1-0.3 microns for typical influenza virus particle (including 0.125 microns for the Coronavirus). The MPPS values may also correspond to one or more specific particle sizes (=/−0.1 to 10% of the nominal value) such as 0.1 micron, 0.15 microns, 0.2 microns, 0.25 microns, 0.3 microns, 0.35 microns, 0.4 microns, 0.5 microns, 1 micron, and fractional and/or integer multiples thereof.

In accordance with a further aspect of the invention, a particular filter layer may substantially or essentially comprise a single material or a plurality of materials. A particular filter layer may be manufactured or assembled using one or more processes including electrospinning, force spinning, and fiber splitting, in addition to or in lieu of woven and non-woven assembly techniques. A particular filter layer may comprise a substantially homogeneous distribution of fiber sizes of substantially the same length L and diameter D (where D may be on the order of 1 micron or greater, sub-micron, or in the range of nano-fibers).

In other embodiments, the layer may comprise a heterogeneous distribution of fiber materials and/or sizes expressed as, for example, "the composition X %+Y % . . . +Z %;" where X+Y . . . +Z=100, and X, Y, . . . and Z represent the relative amounts of the constituent components of the finished filter layer. For example, a layer may comprise 60% fibers of attribute X, 30% fibers of attribute Y, and 10% fibers of attribute Z; where X corresponds to a fiber diameter in the range 1 nanometer, Y corresponds to a fiber diameter in the range of 1 micrometer, and Z corresponds to a fiber diameter in the range of 1 micron. Alternatively, X, Y, and Z may represent a class or type of material such as a natural (e.g., cotton) or synthetic (e.g., a hydrocarbon chain) fiber.

As a further alternative, X, Y, . . . and Z may represent, in addition to or in lieu of the foregoing attributes, one or more material properties of a constituent component of the layer, including physical (e.g., tensile strength, shear strength), chemical (crosslinking or hydrogen bonding sites), and/or electromagnetic properties. In this regard, the present invention further contemplates that a particular filter layer may be cut from a larger sheet of material which itself comprises a single layer. Alternatively, the filter material may comprise one or more layers which may be adjacent and substantially parallel when in a planar orientation, or they may be interwoven, stitched, spot welded, thermally, chemically, and/or mechanically bonded, or otherwise interwoven to form an ordered or unordered matrix.

The various sublayers or subcomponents comprising the resulting filter material may be made from the same or different materials, made from the same or different manufacturing processes, and may comprises different thicknesses and other mechanical properties and may be loosely bound (or not bound at all) to all or a portion of one or more adjacent sublayers. In addition, each layer may be exhibit various degrees and/or combinations of surface features, nano and/or micro-geometric structures, electrostatic properties, surface finishes, surface properties such as tackiness and lubricity, and chemical and/or mechanical affinities to facilitate inter and intra layer bonding or adhesion.

In accordance with a further aspect of the invention, various combinations of the foregoing variables may be employed in an effort to best advance the foregoing design objectives. After measuring and recording the true MPPS values and other reliability and performance metrics, various input and control parameters may be iteratively adjusted in subsequent trials, for example employing machine learning techniques and related models to ultimately yield stable and cost effective protocols (or "recipes") for producing filter materials which reliably and repeatedly exhibit the desired properties, including MPPS values.

Referring now to FIG. 1, a first embodiment of a multi-stage nasal filter assembly 100 comprises all or a subset of a first stage filter 110, a second stage filter 120, and a third stage filter 130. The first stage filter 110 may comprise a disc shaped structure supporting a first filter layer characterized by one or more MPPS values. The second stage filter 120 may partially or wholly comprise a semi rigid or resiliently deformable material such as plastic or nylon.

The second stage filter may also include one or more sub-layers embedded into, circumscribing, or otherwise adjacent to the internal and/or external boundary surfaces of element 120. In addition, one or more of the filter layers may be convoluted; that is, the material may be folded, pleated, or otherwise configured to expand the effective surface area of the material in three dimensions as described in greater detail below in conjunction with FIG. 8.

In this way the second stage may expand when inserted to form a gentle seal along a portion of its exterior perimeter with a corresponding region of the interior nasal walls. At the same time, the second stage filter material (and the other stages as well) may embody the desired MPPS value(s), without the high impedance associated with conventional planar filter layers typically implemented in two-dimensions.

With continued reference to FIG. 1, the interface 115 between the first and second stages may comprise a bearing surface, contactless (a gap), or partial contact between the first and second stages. An air gap 127 between the second and third stages provides a region in which antiseptic liberated from one or more filter layers may be aerosolized due to turbulent air flow, as described in greater detail below in conjunction with FIG. 3. One or more of the filter layers may include N95, N99, N100, or analogous materials of the type used in presently known respirator-type facial masks made by the 3M Company of Saint Paul, Minn.

With continued reference to FIG. 1, second stage filter 120 may be generally cone shaped with a domed terminus, while also exhibiting a generally elliptical cross section to closely mate with the internal nasal cavity upon insertion therein. Prior to insertion, the foam or other resiliently deformable material comprising the second stage filter exhibits a cross-section dimension $d_1$. As described below in connection with FIG. 2, as the device is inserted into and manually guided upwardly into the nostril 200, the second stage filter material compress slightly, and thereafter expands in situ to urge the second and third stage filter radially outwardly against the internal nasal cavity, forming a perimeter seal. (See the interface 125 between the second and third stage filters shown in FIG. 2.) In an alternate embodiment, the distal region of the second stage filter structure may be flared outwardly to provide additional spring force proximate the perimeter seal.

FIG. 2 shows the filter assembly inserted into the nostril between the septum 202 and the nares 204, with the direction of inhaled air flow being indicated by arrows 261 (pre-filter) and 262 (post filter). As shown, the compressed cross-section dimension $d_2$ is slightly less than the uncompressed dimension $d_1$ of FIG. 1. As the antiseptic saturated filter material is inserted, the exposed distal mucosa 252 and 254 are swabbed, providing an antiseptic coating which eliminates (or at least mitigates) the entry vector for pathogens associated with prior art devices. An air gap 290 between the second and third stages is discussed below in connection with FIG. 3.

FIG. 3 schematically illustrates turbulent air flow resulting from venturi-type effects of air flowing through a restricted zone (e.g., the second and/or third stage filters). As shown, an air gap 227 may be formed between the distal surface 331 of the first stage filter and the proximal surface 332 of the third stage filter. In particular, pathogens 301 intermingle with aerosolized droplets 305 in the air gap 227 between the second and third stages, as well as in the region 120 upstream of the second filter, the regions within third stage filter 130 and downstream of the second filter stage, and/or near the proximal surface 333 of the third stage filter.

In an alternate embodiment, a fourth filter stage filter generally similar in size, shape, structure, and function to the third filter stage, may be disposed downstream (during inhalation) of the third stage filter and loosely encapsulating or circumscribing a portion of the third stage (to the right of element 333 in FIG. 3). The fourth stage should be configured to form a substantial gap between the third and fourth stages, and provide a supplemental reservoir of antiseptic to be aerosolized as the airstream leaves the device. The role the fourth stage plays in eliminating harmful particles relies as much or more on chemical mechanisms than mechanical ones. As such, the fourth stage material may suitable exhibit a relatively high MPPS value and correspondingly low impedance.

Figure 4:
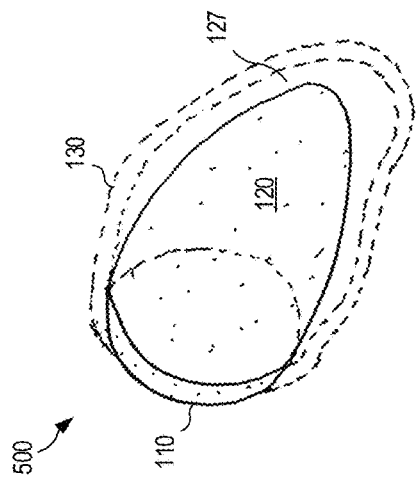
FIG. 4 is a schematic cross-section view of an alternate embodiment of a multi-stage filter in accordance with various embodiments.

FIG. 4 is a schematic cross-section view of an alternate embodiment of a multi-stage filter 400 wherein the outer perimeters of the first stage 110 and the third stage 130 are substantially coextensive proximate their junction.

Figure 5:
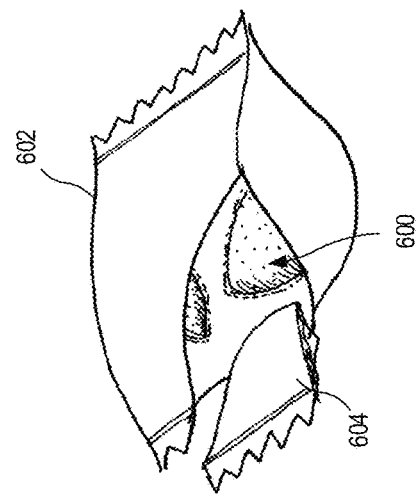
FIG. 5 is a schematic perspective view of a one side of a dual multi-stage nasal filter in accordance with various embodiments.

FIG. 5 is a schematic perspective view of one side 500 of a dual multi-stage nasal filter showing the air gap 127 in three dimensions. In this regard, note that one or more air gaps for facilitating eddy currents and turbulence may be configured to exhibit any desired size or volume.

Figure 6A:
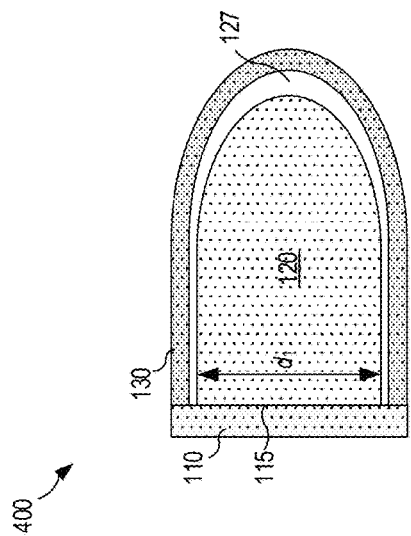

FIG. 6A is a perspective view of a sealed package 602 containing a pair 600 of nasal filters saturated in an aqueous antiseptic solution in accordance with various embodiments.

Figure 6B:
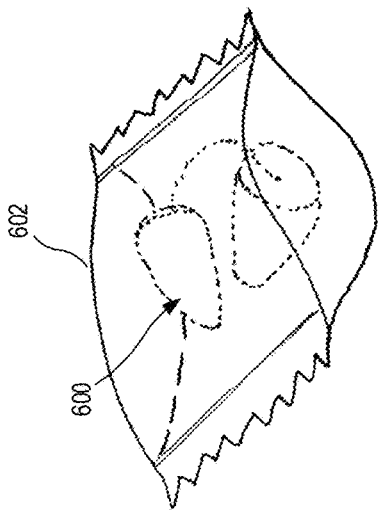

FIG. 6B is a perspective view of the package of FIG. 6A shown torn open by removing segment 604 to reveal the saturated nasal filters.

FIG. 7 illustrates a pair of nasal filters 701, 702 and a band 710 interconnecting the two filters together. In the illustrated embodiment the band 701 is connected to filter 701 at a connection point 721, and the band 701 is connected to filter 702 at a connection point 722. Those skilled in the art will appreciate that the bad may connect to each filter at any convenient point on any desired filter stage.

FIG. 8 depicts a multistage filter device 800 including a first filter stage 810, a second filter stage 822, and a third stage 830. A space 827 may separate the second stage 822 from the third stage 830. A portion of the second stage 822 may abut a portion of the first stage 810 along an interface 815. As shown, the second stage 822 may comprise regular or irregular convolutions 823 (which may optionally yield a hollow portion or internal volume 821). As illustrated, the second stage 822 comprises a hollow interior defining a plurality of concave finger-like convolutions 823, increasing the effective surface area of the filter layer and reducing its impedance.

As shown in FIG. 8, convoluting one or more of the filter stages (or their sub-components) increases the surface area through which ambient air is drawn and expelled, thereby reducing the impedance associated with a non-convoluted version of the same material.

FIG. 9 illustrates an alternate embodiment 900 of the multi-stage filter of FIG. 8, wherein the second stage 920 comprises a "solid" interior terminating in a plurality of convex convolutions 925, resulting in a substantial gap 927 between the ends of the convolutions and the inside surface of the third stage filter layer 930. A resiliently expandable ring 910 may be used to help urge the second (and possibly the first) stage material outwardly against the adjacent nasal wall to form a perimeter seal. The optional ring 910 may be integral to the first stage filter structure, circumscribe the first stage structure, or partially or entirely replace the first stage.

FIG. 10A is a schematic cross-section view of an alternate embodiment 901 of a multi-stage filter similar to FIG. 8 or 9, including an optional, resiliently expandable claw disposed with its convex region extending in the distal direction of the nasal passage. The claw performs a function similar to that performed by ring 910, and may thus be used in addition to or in lieu of the ring. Additionally, as seen in FIG. 11, the claw is non-planar, providing a three-dimensional platform to support a cup-shaped first stage filter layer, if desired. In particular, the hub 912 of the claw provides low impedance support for a center portion of a cup-shaped filter layer, and the spoked extensions 914 provide low impedance structural support for radial portion of the filter layer.

FIG. 10B is a schematic cross-section view of an alternate embodiment 902 of a multi-stage filter similar to FIG. 10, with the resiliently expandable claw disposed with its concave region extending in the distal direction of the nasal passage in accordance with various embodiments; and FIG. 11 is perspective view of the claw shown in FIG. 10

In various embodiments, pore sizes for the materials comprising the filter stages range from 0.001 microns to 1000 microns. Moreover, a particular filter stage may include multiple pore sizes (which may increase turbulence).

Additional embodiments may contemplate a filter wherein a particular stage itself comprises two "stages," wherein the airflow is forced sideways along the inspiration path causing increased interaction with filter walls.

A further embodiment involves a single stage device for allergens, wherein the single stage comprises a compressible foam or other resiliently deformable material with entrained antiseptic.

A method is thus provided for installing a nasal filter device into a nostril, where the device includes a resiliently deformable component and first filter stage having a first filter layer. The method includes: manually opening a sealed envelope containing the device in a liquid antiseptic medium; removing the device from the package; inserting the device into a distal region of the nostril; and urging the device from the distal region upwardly into the nostril while simultaneously swabbing the distal region with liquid antiseptic medium present on the perimeter of the deformable component.

In an embodiment, the first filter layer is characterized by a most penetrating particle size (MPPS1) value in the range of 0.1 to 0.3 micrometers (um).

In an embodiment, the first filter layer is characterized by a most penetrating particle size (MPPS1) value of about 0.125 micrometers (um).

In an embodiment, the liquid medium comprises at least one of an antiseptic and a disinfectant, and wherein swabbing comprises rotating the deformable component against the distal region of the nostril while urging the device upwardly.

In an embodiment, the first filter layer comprises electrostatic material.

In an embodiment, the first filter layer comprises an electrospun material.

In an embodiment, the first filter layer comprises three dimensional convolutions.

In an embodiment, the nostril is characterized by a cross-sectional area of about K (inches)2; and the convolutions are configured to impart an effective cross-sectional surface area to the first filter layer of at least 2k, and in some cases 10k.

In an embodiment, the method further includes: leaving the device within the nostril for a period of time in the range of one to six hours; and thereafter removing the device from the nostril.

In an embodiment, the first filter layer is further characterized by two different values MPPS1 and MPPS1.2

In an embodiment, the device further comprises a second filter stage having a second filter layer is characterized by a second MPPS2 value.

In an embodiment, the second filter layer comprises electrospun fibers having diameters in the submicron range.

A nasal filter device is also provided for insertion into a nostril having an internal nostril circumference. The device includes: a first stage having a first filter layer; and a second stage having a second filter layer characterized by an MPPS2 value.

In an embodiment, the second filter layer comprises an electrospun material.

In an embodiment, the nostril is characterized by a cross-sectional area of about K (inches)2; and the second filter layer comprises convolutions configured to impart an effective cross-sectional surface area to the second filter layer of at least 2k, potentially 10k.

In an embodiment, the second stage comprises a resiliently deformable component configured to swab the distal region of the nostril interior with a disinfectant during device installation.

In an embodiment, the device further includes a third stage having a third filter layer characterized by an MPPS3 value.

In an embodiment, the third filter layer comprises an electrospun material, and wherein MPPS3 value is different from the MPPS2 value.

In an embodiment, the third filter layer comprises a flexible sheet loosely enveloping at least a portion of the second stage and forming an air gap therebetween; and the device includes a spring element configured to urge the distal portion of the second stage outwardly to form a perimeter seal with the inside of the nostril.

A nasal filter device is also provided, comprising: a resiliently deformable element configured to form a perimeter seal with the inner nostril wall and to swab the distal portion of the internal nostril region with a disinfectant during device installation; a first filter stage having a first filter layer characterized by first geometric convolutions and a first MPPS1 value; and a second filter stage having a second filter layer characterized by second geometric convolutions and a second MPPS2 value A method is also provided for impeding the inhalation of particulates using a resiliently deformable filter packaged in a sealed envelope containing a liquid medium. The method includes: opening the sealed package to thereby expose the filter to ambient air; removing the filter from the package; inserting the filter into a distal region of a nostril; and urging the filter from the distal region to a proximal region of the nostril while simultaneously swabbing the distal region with liquid medium present on the perimeter of the filter.

In an embodiment, the filter is characterized by a mean pore size in the range of 0.1 to 100 micrometers (um), and preferably 0.5 to 50 um, and most preferably 0.1 to 10 um.

In an embodiment, the particulates comprise allergens, and further wherein the filter is characterized by a mean pore size in the range of 3 to 7 um.

In an embodiment, the liquid medium comprises an antiseptic.

In an embodiment, the liquid medium comprises a disinfectant.

In an embodiment, the particulates comprise microorganisms.

In an embodiment, the particulates comprise allergens.

In an embodiment, the filter comprises electrostatic material.

In an embodiment, the liquid medium comprises povidone iodine.

In an embodiment, swabbing comprises rotating the filter within the distal region of the nostril.

In an embodiment, swabbing comprises simultaneously rotating and urging the filter upwardly within the nostril.

In an embodiment, the method further includes: leaving the filter within the proximal region for a period of time in the range of five minutes to eighteen hours; and thereafter removing the filter from the nostril.

In an embodiment, the method further includes: leaving the filter within the proximal region for a period of time in the range of one to six hours; and thereafter removing the filter from the nostril.

In an embodiment, the filter further comprises a pair of filters connected by a band.

In an embodiment, the method further includes removing the pair of filters from respective nostrils by manually pulling on the band.

In an embodiment, the filter further includes: an initial stage characterized by a first pore size; an intermediate stage characterized by a second pore size; and a final stage characterized by a third pore size; wherein the third pore size is a smaller than the first and second pore sizes.

A nasal filter is provided for insertion into a nostril having an internal nostril circumference. The filter includes: an initial stage characterized by a first pore size; an intermediate stage characterized by a second pore size; and a final stage characterized by a third pore size; wherein the third pore size is a smaller than the first and second pore sizes.

In an embodiment, the initial stage comprises a perimeter ring supporting a substantially planar filter material; the intermediate stage comprises a resiliently deformable filter material having a substantially flat distal end adjacent the initial stage and a dome shaped proximal end; and the final stage comprises a sheet of fabric loosely enveloping the intermediate stage and forming an air gap therebetween.

In an embodiment, at least one of the initial, intermediate, and final stages comprise an antiseptic coating.

In an embodiment, the resiliently deformable filter material is configured to urge the sheet of fabric against internal nostril circumference.

The description of exemplary embodiments of various filter stages and their materials and functions is merely exemplary and is intended for purposes of illustration only; the following description is not intended to limit the scope of the disclosure or the claims. Moreover, recitation of multiple embodiments having stated features, compositions, or properties is not intended to exclude other embodiments having additional features, compositions, or properties, or other embodiments incorporating different combinations of the stated features, compositions, or properties, unless otherwise noted herein.

Although exemplary embodiments of the present disclosure are set forth herein, it should be appreciated that the disclosure is not so limited. For example, although materials, media, apparatus, systems, and methods are described in connection with multi-stage filters, the invention may also be used in the context of single stage filters. Various modifications, variations, and enhancements of the materials, methods, and media set forth herein may be made without departing from the spirit and scope of this disclosure.

The invention claimed is:

1. A method of installing a nasal filter device into a nostril, where the device includes a resiliently deformable component and first filter stage, the method comprising:
    manually opening a sealed envelope containing the device in a liquid antiseptic medium;
    removing the device from the package;
    inserting the device into a distal region of the nostril; and
    urging the device from the distal region upwardly into the nostril while simultaneously swabbing the distal region with liquid antiseptic medium present on the perimeter of the deformable component;
    wherein the first filter stage includes a first layer comprising a plurality of folded geometric features forming concave, three dimensional finger-like geometric convolutions.

2. The method of claim 1 wherein the first filter layer is characterized by a most penetrating particle size (MPPS1) value in the range of 0.1 to 0.3 micrometers (um).

3. The method of claim 1 wherein the first filter layer is characterized by a most penetrating particle size (MPPS1) value of about 0.125 micrometers (um).

4. The method of claim 1 wherein the liquid medium comprises at least one of an antiseptic and a disinfectant, and wherein swabbing comprises rotating the deformable component against the distal region of the nostril while urging the device upwardly.

5. The method of claim 1 wherein the first filter layer comprises electrostatic material.

6. The method of claim 1 wherein the first filter layer comprises an electrospun material.

7. The method of claim 1 wherein:
    the nostril is characterized by a cross-sectional area of about K (inches); and
    the convolutions are configured to impart an effective cross-sectional surface area to the first filter layer of at least 2k.

8. The method of claim 1 further comprising:
    leaving the device within the nostril for a period of time in the range of one to six hours; and
    thereafter removing the device from the nostril.

9. The method of claim 1 wherein the first filter layer is further characterized by two different values MPPS1 and MPPS1.2.

10. The method of claim 1 wherein the device further comprises a second filter stage having a second filter layer is characterized by a second MPPS2 value.

11. The method of claim 10 wherein the second filter layer comprises electrospun fibers having diameters in the sub-micron range.

* * * * *